United States Patent [19]

Kolar et al.

[11] Patent Number: 4,719,289
[45] Date of Patent: Jan. 12, 1988

[54] GLYCOPEPTIDES, PROCESS FOR THEIR PREPARATION AND THEIR USE

[75] Inventors: Cenek Kolar; Friedrich R. Seiler, both of Marburg; Ursula Knödler, Ebsdorfergrund, all of Fed. Rep. of Germany

[73] Assignee: Behringwerke Aktiengesellschaft, Fed. Rep. of Germany

[21] Appl. No.: 776,380

[22] Filed: Sep. 16, 1985

[30] Foreign Application Priority Data

Sep. 17, 1984 [DE] Fed. Rep. of Germany ....... 3434039

[51] Int. Cl.$^4$ .......................... C07K 5/06; C07K 5/08; C07H 5/04
[52] U.S. Cl. .................................. 530/331; 536/18.7
[58] Field of Search ...................... 530/331; 536/18.7

[56] References Cited

FOREIGN PATENT DOCUMENTS 96293 5/1983 European Pat. Off. .

OTHER PUBLICATIONS

Chem. Abstr., vol. 93, (1980), 132758.
Chem. Abstr., vol. 89, (1978), 75448.
Chem. Abstr., vol. 104, (1986), 149364.
Carbohydrate Res., 79, (1980), C1–C7.
Carbohydrate Res., 76, (1979), 85–89.
The Journal of Biological Chem., 258, (1983), 11537–11545.
Carbohydrate Research, 116 (1983), Seiten C9–C12.
Carbohydrate Research, Band 79 (1980), Seiten C1–C7.

*Primary Examiner*—Delbert R. Phillips
*Attorney, Agent, or Firm*—Finnegan, Henderson, Farabow, Garrett & Dunner

[57] ABSTRACT

Compounds of the general formula I, II or III $$R^1-A^1-T-NH-R^2-COR^3 \quad \quad I$$

$$R^1-A^1-T-A^2-NH-R^2-COR^3 \quad \quad II$$

$$R^1-A^1-T-A^2-A^3-T-A^4-NH-R^2-COR^3 \quad \quad III$$

are described, in which $R^1$ is a hydrogen atom, an alkoxycarbonyl or arylalkoxycarbonyl group conventionally used for protecting amino groups, or $CH_3-(CH_2)_m-CO$, in which $m=0-16$, $R^2$ is $-(CH_2)_n-$ or $-(CHOH)_n-$, in which $n=1-10$, $R^3$ is a hydroxyl group, an 0-alkyl or 0-arylalkyl protecting group, a group which activates carboxyl groups, a cephalin radical, an amino acid radical of oligopeptides, polypeptides or proteins which carries NH groups, or a carrier, $A^1$, $A^2$, $A^3$ or $A^4$ is a bonding dash or an amino acid radical present in glycophorin A, such as Ala, Val, Leu, Ile, Ser, Pro, Glu or Arg, in which, if appropriate, the reactive groups not forming part of the peptide bond are protected by protecting groups, and the radical T is t,0010 in which $R^4$ denotes a hydrogen atom or an acyl protecting group, $R^5$ denotes a hydrogen atom, an acyl protecting group or the 2,3,4,6-tetra-0-acetyl-beta-D-galactopyranosyl or beta-D-galactopyranosyl radical, $R^6$ denotes $N_3$, $NH_2$ or NHAc and $R^7$ denotes H or $CH_3$, together with a process for their preparation and their use, bound to a carrier, as artificial antigens, glycolipids or immunoadsorbents.

6 Claims, No Drawings

GLYCOPEPTIDES, PROCESS FOR THEIR PREPARATION AND THEIR USE

The invention relates to compounds of the general formula I, II or III $$R^1-A^1-T-NH-R^2-COR^3 \quad \text{I}$$

$$R^1-A^1-T-A^2-NH-R^2-COR^3 \quad \text{II}$$

$$R^1-A^1-T-A^2-A^3-T-A^4-NH-R^2-COR^3 \quad \text{III}$$

in which
$R^1$ denotes a hydrogen atom, an alkoxycarbonyl or arylalkoxycarbonyl group conventionally used for protecting amino groups, or $CH_3-(CH_2)_m-CO$, in which $m=0-16$,
$R^2$ denotes $-(CH_2)_n-$ or $-(CHOH)_n-$, in which $n=1-10$,
$R^3$ denotes a hydroxyl group, an O-alkyl or O-arylalkyl protecting group, a group which activates carboxyl groups, a cephalin radical, an amino acid radical of oligopeptides, polypeptides or proteins which carries NH groups, or a carrier,
$A^1$, $A^2$, $A^3$ or $A^4$ denotes a valency bond or an amino acid radical present in glycophorin A, such as Ala, Val, Leu, Ile, Ser, Pro, Glu or Arg, in which, if appropriate, the reactive groups not forming part of the peptide bond are protected by protecting groups, and the radical T denotes

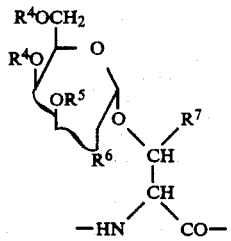

in which
$R^4$ is a hydrogen atom or an acyl protecting group,
$R^5$ is a hydrogen atom, an acyl protecting group or the 2,3,4,6-tetra-O-acetyl-beta-D-galactopyranosyl or beta-D-galactopyranosyl radical,
$R^6$ is $N_3$, $NH_2$ or NHAc and
$R^7$ is a hydrogen atom or a methyl group,
and also to a process for their preparation and their use, bound to a carrier, as artificial antigens, glycolipids or immunoadsorbents.

The treatment of erythrocytes of the M or N blood group with neuraminidase involves exposing the so-called Thomsen-Friedenreich (T) antigen. This T antigen has been characterized as the disaccharide unit -D-Gal-(1-3)-alpha-D-GalNac, which is incorporated in the polypeptide chain of proteins via L-serine or L-threonine radicals. The $T_N$ antigen is obtained by cleavage of the -O-glycosidically bonded galacto unit.

The T or $T_N$ antigen structures are present in, for example, the major glycoprotein of the erythrocyte membrane—namely the glycophorin—as "cryptoantigens".

However, in the tumor tissue of various types of cancer, Springer (Naturwissenschaften (1983) 70, 369) has also been able to detect T and $T_N$ antigen structures, so these are to be regarded as tumor-associated antigens.

Although the carbohydrate part of the T and $T_N$ antigen structures is characterized, the oligopeptide part is not.

Uhlenbruck et al., Immunbiol, (1983), 165, 147, have proved that a glycopeptide structure is responsible for the specificity of the T determinant. As glycopolypeptides isolated from glycophorin were used for this work, the T and $T_N$ specificity could not be explained. Through the chemical synthesis of relevant glycopeptides whose serological and immunochemical properties are comparable to those of the natural T-specific structures, it would be possible to characterize the complete structure of the Thomsen-Friedenreich determinant and the T-specific tumor-associated determinant.

Glycopeptide inhibitors, artificial antigens or immunoadsorbents with structures of the T-specific and $T_N$-specific determinants are prepared using chemical compounds with these structural features, which can be reacted with suitable carrier molecules. It would be possible to use synthetic T-specific and $T_N$-specific antigens to obtain corresponding antibodies. These specific antibodies could be used for the diagnosis and early detection of cancer.

The preparation of glycopeptides or synthetic antigens is usually accompanied by the difficulties associated with the protecting group chemistry of carbohydrates and peptides. Although Ferrari and Pavia (Carbohydrate Research (1980), 79, C1-C7) were able to synthesize an alpha-D-GalNac-L-serine or L-threonine segments, attempts to remove a methyl ester protecting group were unsuccessful, making this segment unsuitable for the preparation of glycooligopeptides. Although Paulsen (Chemical Society Reviews (1984), Volume 13, No. 1, 15) and Sinay et al. (Carbohydrate Research (1983), 116/2, C9) were able to synthesize terminal glycopeptides as segments of the glycophorin, these glycopeptides do not correspond to the T and $T_N$ specificity, as Uhlenbruck was able to prove.

Surprisingly, it has now been shown that the unprotected glycopeptides of the formulae I and II, and especially of the formula III, have serological T or $T_N$ activity which is comparable to asialoglycophorin. It has also been shown, surprisingly, that glycopeptide haptens which contain two ester groups can be coupled with carrier molecules selectively via the carboxyl group of the spacer. This opens up a new route to the preparation of complex glycopeptide antigens.

The object of the present invention was to prepare glycopeptides capable of coupling, from which artificial T-active and $T_N$-active antigens, immunoadsorbents or glycolipids can be prepared by being covalently bonded to carriers. This object is achieved by preparing compounds of the general formulae I, II and III, defined as indicated above, and binding them to carriers.

Preference is given to compounds which are present as partial structures in glycophorin, of the

| | |
|---|---|
| $R^1-Leu-T-NH(CH_2)_5-COR^3$ | formula V |
| $R^1-Ser-T-NH(CH_2)_5-COR^3$ | formula VI |
| $R^1-Ile-T-Ser-NH(CH_2)_5-COR^3$ | formula VII |
| $R^1-Pro-T-Ala-NH(CH_2)_5-COR^3$ | formula VIII |
| $R^1-Val-T-Glu(R^9)-NH(CH_2)_5-COR^3$ | formula IX |

$R^1$—Ile—T—Val—NH(CH$_2$)$_5$—COR$^3$      formula X $R^1$—Arg(R$^{10}$)—T—Val—NH(CH$_2$)$_5$—COR$^3$      formula XI $R^1$—Ala—T—Pro—NH(CH$_2$)$_5$—COR$^3$      formula XII $R^1$—Val—T—Glu(R$^9$)—Ile—T—Val—NH(CH$_2$)$_5$—COR$^3$      formula XIII $R^1$—Ile—T—Val—Arg(R$^{10}$)—T—Val—NH(CH$_2$)$_5$—COR$^3$      formula XIV in which $R^1$ denotes a hydrogen atom or an acetyl group, $R^3$ denotes a hydroxyl group, OCH$_3$, O-tert.-butyl, O-benzyl, an active ester, a polylysine, protein or cephalin radical, a gel which carries amino groups, or a carrier, $R^9$ denotes a hydrogen atom or a protecting group for carboxyl groups, such as the methyl, benzyl or tert.-butyl group, $R^{10}$ denotes a hydrogen atom or a protecting group for amino groups, such as the NO$_2$ group, and T has the meaning given below.

In the process for the preparation of one of the compounds of the formulae I, II and III, (a) a compound of the general formula XV

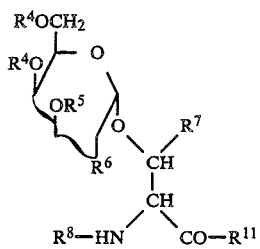

in which $R^4$ denotes an acyl protecting group, preferably an acetyl or benzoyl group, $R^5$ denotes an acyl protecting group or a 2,3,4,6-tetra-O-acetyl-beta-D-galactopyranosyl radical, $R^6$ denotes N$_3$ or NHAc, $R^7$ denotes H or CH$_3$, $R^8$ denotes an alpha,alpha-dimethyl-3,5-dimethoxybenzyloxycarbonyl, benzyloxycarbonyl or 9-fluorenylmethoxycarbonyl group and $R^{11}$ denotes O—CH$_2$Ph, is hydrogenated in the presence of a hydrogenation catalyst such as palladium/charcoal, and in the presence of an organic solvent such as methanol, ethyl acetate or diethyl ether, at room temperature, and, if appropriate, the free alpha-amino group of the serine or threonine blocked with an alkoxycarbonyl or arylalkoxycarbonyl protecting group, preferably DDZ, Z, BOC or Fmoc, thereby forming a compound of the general formula XV in which the radicals $R^4$, $R^5$, $R^6$ and $R^7$ retain the meanings given above, $R^8$ is a DDZ, Z, BOC or Fmoc group and $R^{11}$ is a hydroxyl group, (b) the product of step (a) is reacted, by a condensation process conventionally used in peptide chemistry, such as the dicyclohexylcarbodiimide or active ester process, or using succinimide esters or p-nitrophenyl esters or mixed anhydrides, with a compound of the general formula XVI, which has a free amino group

H—A—NH—R$^2$—COR$^3$      XVI in which

A denotes a valency bond or an amino acid radical, preferably Ala, Val, Pro, Ser, (benzyl)Ser, Glu(gamma-tert.-butyl) or Glu(gamma-Bn), $R^2$ denotes —(CH$_2$)$_n$—, in which n=1–10, and $R^3$ denotes OCH$_3$, O-benzyl or O-tert.-butyl, or with a compound of the general formula XVII H—A$^2$—A$^3$O—benzyl      XVII in which A$^2$ is Ala, Val, Pro, Ser, (benzyl)Ser, Glu(gamma-tert.-butyl), Glu(gamma-methyl) or Glu(gamma-Bn) and A$^3$ is a valency bond or an amino acid radical Ile or (NO$_2$)Arg, to give a compound of the general formula XV in which the radicals $R^4$, $R^5$, $R^6$, $R^7$ and $R^8$ are unchanged and $R^{11}$ denotes A—NH—R$_2$—COR$^3$ or A$^2$—A$^3$—O—benzyl, the radicals A, A$^2$, A$^3$, $R^2$ and $R^3$ being unchanged.

(c) the protecting group DDZ, BOC, Z or Fmoc in a product of step (b) is selectively cleaved by hydrolysis or hydrogenolysis, in a manner known per se, and the intermediate formed, which carries alpha-amino groups, is reacted with a compound of the general formula XVIII

R$^1$—A$^1$—OR$^{12}$      XVIII in which $R^1$ denotes an acetyl group or a protecting group such as the DDZ, BOC, Z or Fmoc group, A$^1$ denotes a radical of one of the amino acids Ala, Val, Ile, Pro, Arg or (NO$_2$)Arg and R$^{12}$ denotes a hydrogen atom or an active ester radical such as the N-succinylimide or p-nitrophenyl radical, by the condensation process conventionally used in peptide chemistry, to give a compound of the general formula I or II in which $R^1$ is an acetyl group or a DDZ, BOC, Z or Fmoc group, $R^2$ is —(CH$_2$)$_n$—, in which n=1–10, $R^3$ is OCH$_3$, O-benzyl or O-tert.-butyl, A$^1$ is one of the amino acid radicals indicated and T is a radical of the formula XV with the meaning indicated under process step (a), $R^8$ and $R^{11}$ together being a valency bond or to give a compound of the general formula XIX R$^1$—A$^1$—T—A$^2$—A$^3$—O—benzyl      XIX in which $R^1$, A$^1$, A$^2$, A$^3$ and T have the last meanings indicated, (d) the benzyl group in the product of the general formula XIX is selectively cleaved by hydrogenolysis and the product is reacted, by one of the condensation methods conventionally used in peptide chemistry, with a compound of the general formula XX

H—A$^3$—T—A$^4$—NH—R$^2$—COR$^3$      XX in which A$^3$, A$^4$, T, R$^2$ and R$^3$ have the last meanings mentioned, to give a compound of the general formula III, (e) the protecting groups in a product of step (c) or (d) are removed by processes conventionally used in carbohydrate chemistry or peptide chemistry and the free amino group on the galactosaminyl radical is selectively acetylated, a product of the general formula I, II or III being formed in which $R^1$ denotes an acetyl group or a protecting group,
$R^2$ denotes $-(CH_2)_n-$, in which $n=1-10$,
$R^3$ denotes a hydroxyl group,
T denotes the radical mentioned at the outset, in which $R^4$ is a hydrogen atom, $R^5$ is a hydrogen atom or a D-galactopyranosyl radical, $R^6$ is NHAc and $R^7$ is H or $CH_3$, and
$A^1$, $A^2$, $A^3$ and $A^4$ have the last meanings mentioned, (f) a product of step (e) is reacted in a manner known per se, by a conventional condensation process, with a polymeric compound which carries amino groups, or a carrier, such as polylylsine, cephalin, a protein or a gel, to give a synthetic glycolipid, antigen or immunoadsorbent, and (g) if appropriate, the remaining protecting groups in a product of step (f) are removed in a manner known per se, by deblocking processes conventionally used in peptide chemistry.

The glycopeptides and glycopeptide derivatives of the general formulae I, II and III are prepared by a process conventionally used in peptide chemistry, for example in Houben-Weyl, Methoden der organischen Chemie (Methods of organic chemistry), Volume XV/1 and 2.

The activation of the carboxyl group can be effected for example by converting the carboxyl group to an acid halide, an azide, an anhydride, an imidazolide or an activated ester such as the N-hydroxysuccinimide ester or the p-nitrophenyl ester.

The amino group can be activated by conversion to a phosphitamide or by the phosphorazo process.

The conventional processes for the abovementioned condensation reactions are: the carbodiimide process, the azide process, the mixed anhydride process and the activated ester process, as described in "The Peptides", Volume 1, 1965 (Academic Press).

The reactive groups which are not intended to take part in the condensation reaction are protected by protecting groups which can easily be removed later, for example by hydrolysis or reduction. Examples of protecting groups are also described in "The Peptides".

It is particularly advantageous also to protect the hydroxyl group of the serine radical. Protecting groups in this context are the benzyl or tert.-butyl group. It is particularly advantageous also to protect the guanidine group of arginine. A conventional protecting group in this context is the nitro group.

Protection of the omega-carboxyl group of glutamic acid is also advantageous. Conventional protecting groups in this context are a tert.-butylcarbonyl, benzyl or methyl group.

The protecting groups can be cleaved by conventional processes according to the particular group, for example with trifluoroacetic acid or by mild reduction for example with hydrogen and a catalyst such as palladium, or with HBr in glacial acetic acid.

The protecting groups on the carbohydrate segment can be cleaved by conventional processes according to the type of protecting group (Angew. Chem. (1982), 94, 184; Carbohydr. Res. (1983), 116, C9–C12). The azido group can be converted to an amino group by mild reduction, for example with hydrogen and a catalyst such as palladium, or with sodium borohydride in the presence of nickel(II) chloride, and the amino group is converted to the acetylamino group by acetylation, for example with acetic anhydride in methanol. The O-acyl protecting groups are advantageously cleaved in a basic medium, for example by means of sodium methylate in methanol or sodium hydroxide or sodium carbonate in methanol.

The glycopeptides of the formulae I, II and III are converted on the carboxyl group of the "spacer portion", by a variety of customary processes, to active ester derivatives such as the N-hydroxysuccinimide ester of the p-nitrophenyl ester, and coupled with a carrier possessing one or more amino groups. Here, the reactive groups of a glycopeptide of the formula I, II or III which are not intended to take part in the condensation reaction are particularly advantageously protected by protecting groups. In particular, the alpha-amino group of the terminal amino acid of the glycopeptide should be protected by a protecting group such as the 9-fluorenylmethoxycarbonyl (Fmoc), alpha,alpha-dimethyl-3,5-dimethoxybenzyloxycarbonyl (DDZ) or tert.-butoxycarbonyl (BOC) group. The protecting groups can easily be removed later, for example by hydrolysis or photolysis.

The binding of haptens to carriers is described, for example, in German Pat. No. 32 30 427. Examples of carriers are proteins, preferably human or bovin serum albumin, glycoproteins, polymers such as polylysine or poly(glycyllysine), activated gels carrying amino, glycidyl, 2-aminoethylamino or active ester groups, polysaccharides or polysaccharide gels activated by cyanogen bromide, or lipids, preferably cephalins or aminated phospholipids.

These glycopeptide derivatives bound to carriers can be used as artificial antigens, glycolipids or immunoadsorbents.

The following should be noted with respect to the various abbreviations used in the description, the examples and the claims:

I. If no optical configuration is given for amino acid radicals, the L form is intended.

II. The following abbreviations are used to denote protecting groups or activating groups:
Adoc = adamantyloxycarbonyl
Fmoc = 9-fluorenylmethoxycarbonyl
DDZ = alpha,alpha-dimethyl-3,5-dimethoxybenzyloxycarbonyl
Z = benzyloxycarbonyl
BOC = tert.-butoxycarbonyl
But$^t$ = tert.-butyl
Me = methyl
OPN = p-nitrophenyl
Bn = benzyl
Bz = benzoyl
Ac = acetyl
DDBn = alpha,alpha-dimethyl-3,5-dimethoxybenzyl
Gal = D-galactopyranosyl
GalNAc = N-acetyl-D-galactopyranosyl The structure of the following compounds was determined by $^1H$ and $^{13}C$ NMR spectroscopy and IR spectroscopy and also by means of elemental analysis. The optical rotations were also determined.

The course of the reactions and the resulting products were investigated by thin layer chromatography and by the HPLC technique.

The examples which follow illustrate the invention in greater detail without thereby implying a limitation.

EXAMPLE 1

Preparation of Compounds of the General Formula I

Scheme 1 below describes the preparation of Compounds 7 and 8. The general procedures are described in the experimental section which follows.

N-Acetyl-L-alanyl-(O-(2-acetamido-2-deoxy-alpha-D-galactopyranosyl)-L-threonyl-N-(5-methoxycarbonyl)-n-pentylamide (Compound 7)

L-Alanyl-(O-(2-acetamido-2-deoxy-alpha-D-galactopyranosyl)-L-threonyl-N-(5-methoxycarbonyl)-n-pentylamide (Compound 8)

The following compounds of the formula I were prepared starting from a compound of the general formula XV as shown in scheme 1.

| Compound No. | $R^1$ | $A^1$ | T | $R^3$ |
|---|---|---|---|---|
| 9 | H | Leu | α-GalNAc—Ser | OBn |
| 10 | Ac | Leu | α-GalNAc—Ser | OBn |
| 11 | H | Leu | β-Gal(1-3)-α-GalNAc—Ser | $OCH_3$ |
| 12 | Ac | Leu | β-Gal(1-3)-α-GalNAc—Ser | $OCH_3$ |
| 13 | H | Ser | β-Gal(1-3)-α-GalNAc—Ser | $OCH_3$ |
| 14 | Ac | Ser | β-Gal(1-3)-α-GalNAc—Ser | $OCH_3$ |

$T^1_{N3}$ = 0-(3,4,6-tri-O-acetyl-2-azido-2-deoxy-alpha-D-galactopyranosyl)

$T^1_{NHAc}$ = O-(2-acetamido-3,4,6-tri-O-acetyl-2-deoxy-alpha-D-galactopyranosyl)

$T_t$ = O-(2-acetamido-2-deoxy-alpha-D-galactopyranosyl)-L-threonyl

EXAMPLE 2

Preparation of Compounds of the General Formula II

Scheme 2 below describes the preparation of Compounds 21 and 22.

L-Isoleucyl-(O-(3-O-(2,3,4,6-tetra-O-acetyl-D-galactopyranosyl)-2-acetamido-4,6-di-O-benzoyl-2-deoxy-alpha-D-galactopyranosyl)-L-seryl-L-valyl-N-(5-benzyloxycarbonyl)-n-pentylamide (Compound 21)

N-Acetyl-L-isoleucyl-(O-(2-acetamido-2-deoxy-3-O-(-D-galactopyranosyl)-alpha-D-galactopyranosyl)-L-valyl-N-(5-benzyloxycarbonyl)-n-pentylamide (Compound 22)

The following compounds of the formula II were prepared starting from a compound of the general formula XV as shown in scheme 2.

Scheme 1

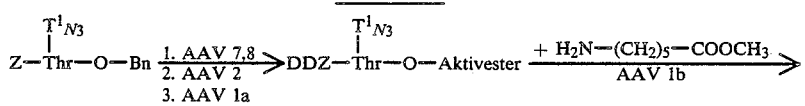

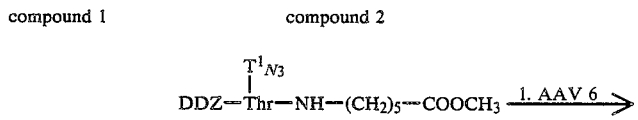

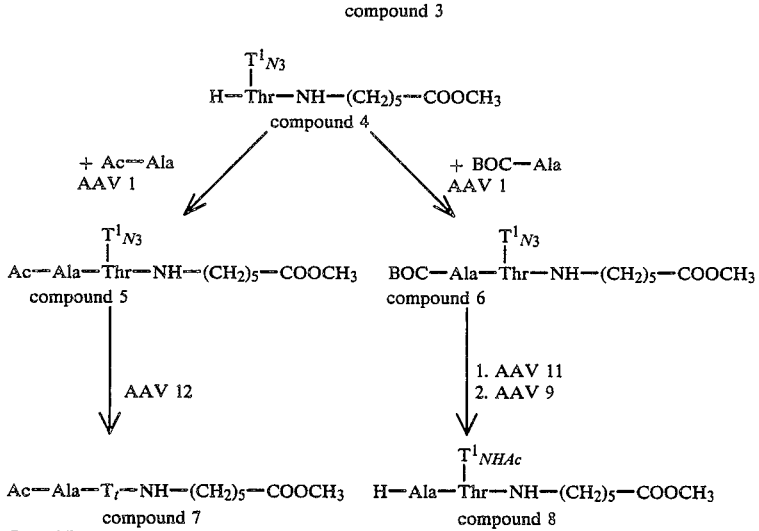

(GP = General Procedure)

| Compound No. | $R^1$ | $A^1$ | T | $A^2$ | $R^3$ |
|---|---|---|---|---|---|
| 23 | Ac | Ile | α-GalNAc-Ser | Ser | $OCH_3$ |
| 24 | Ac | Ile | β-Gal(1-3)-α-GalNAc-Ser | Ser | $OCH_3$ |
| 25 | Ac | Pro | β-Gal(1-3)-α-GalNAc-Thr | Ala | OBn |
| 26 | H | Val | β-Gal(1-3)-α-GalNAc-Ser | Glu(γ-But$^t$) | OBn |
| 27 | Ac | Val | β-Gal(1-3)-α-GalNAc-Ser | Glu(γ-But$^t$) | OBn |

-continued

| Compound No. | R¹ | A¹ | T | A² | R³ |
|---|---|---|---|---|---|
| 28 | Ac | Val | β-Gal(1-3)-α-GalNAc-Ser | Glu | OBn |
| 29 | Ac | Arg | β-Gal(1-3)-α-GalNAc-Thr | Val | OCH₃ |
| 30 | Ac | Ala | β-Gal(1-3)-α-GalNAc-Thr | Pro | OBn |

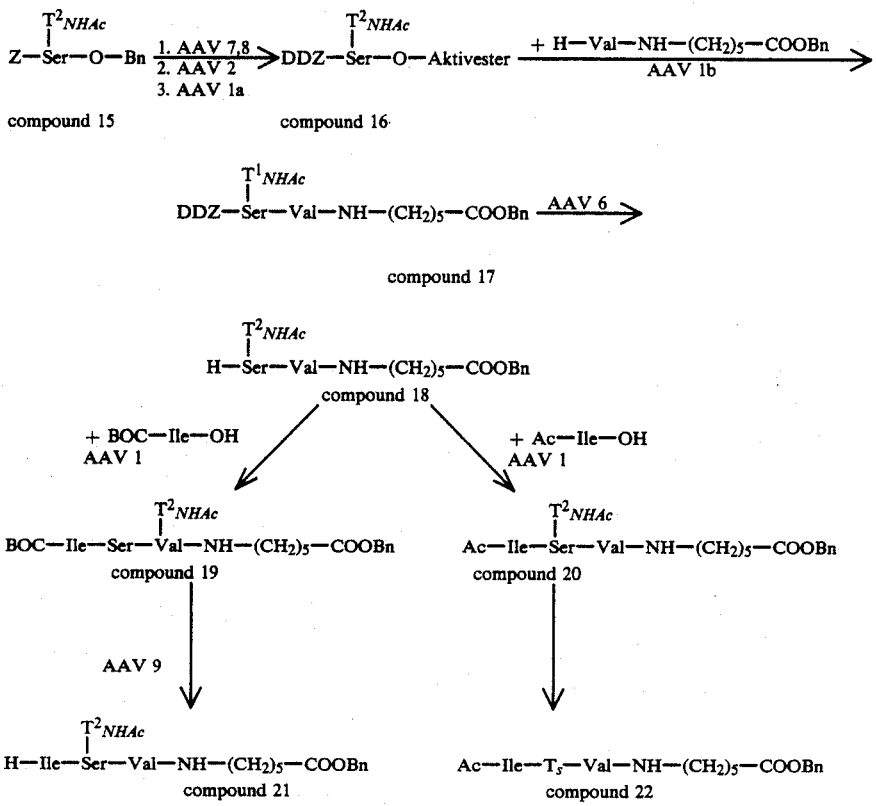

$T^2_{NHAc}$=O-(3-O-(2,3,4,6-tetra-O-acetyl-D-galactopyranosyl)-2-acetamido-4,5-di-O-benzoyl-2-deoxy-alpha-D-galactopyranosyl)

$T_s$=O-(2-acetamido-2-deoxy-3-O-(-D-galactopyranosyl)-alpha-D-galactopyranosyl)-L-seryl

EXAMPLE 3
Preparation of Compounds of the General formula III $$R^1-A^1-T-A^2-A^3-T-NH-(CH_2)_5-COR^3 \quad \text{III}$$

Scheme 3 below describes the preparation of Compound 36.
N-Acetyl-L-valyl-(O-(2-acetamido-2-deoxy-3-O-(-D-galactopyranosyl)-alpha-D-galactopyranosyl)-L-seryl-L-glutamyl-(gamma-tert.-butyl)-L-isoleucyl-(O-(2-acetamido-2-deoxy-3-O)-(-D-galactopyranosyl)-alpha-D-galactopyranosyl))-L-seryl-L-valyl-N-(5-benzyloxycarbonyl)-n-pentylamide (Compound 36)

The following compounds of the formula III were prepared starting from a compound of the general formula XV as shown in scheme 3.

| Compound No. | R¹ | A¹ | T | A² | A³ | A⁴ | R³ |
|---|---|---|---|---|---|---|---|
| 37 | Ac | Val | β-Gal(1-3)-α-GalNAc | Glu | Ile | Val | OBn |
| 38 | Ac | Val | β-Gal(1-3)-α-GalNAc | Glu(γ-Butᵗ) | Ile | Val | OBn | and
N-acetyl-L-isoleucyl-(O-(2-acetamido-2-deoxy-3-O-(-D-galactopyranosyl)-alpha-D-galactopyranosyl)-L-seryl-L-valyl-L-arginyl-(O-(2-acetamido-2-deoxy-3-O)-(-D-galactopyranosyl)-alpha-D-galactopyranosyl))-L-threonyl-L-valyl-N-(5-benzyloxycarbonyl)-n-pentylamide (Compound 39)

Scheme 3

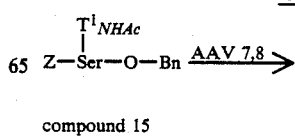

compound 15

-continued
Scheme 3

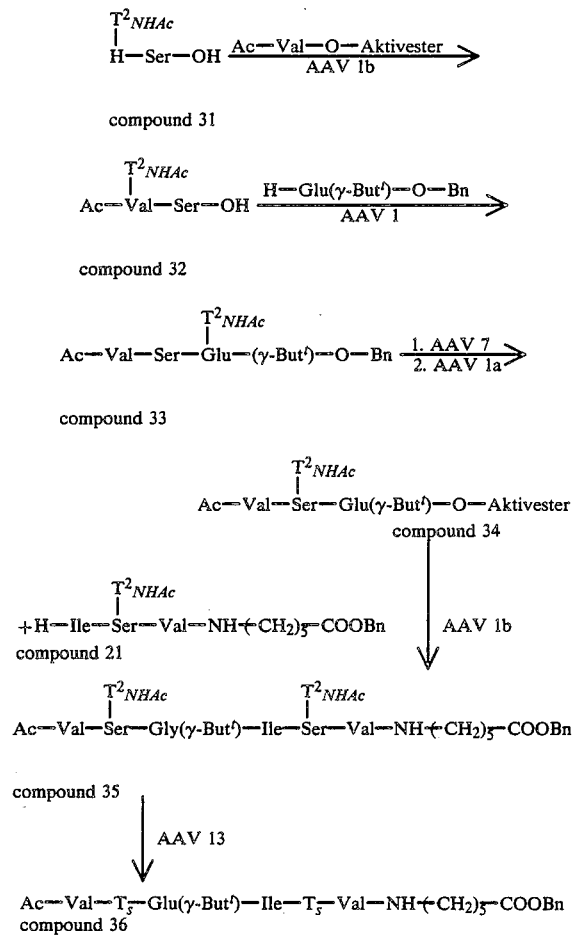

compound 31 compound 32 compound 33 compound 34 compound 21 compound 35 compound 36

$T^2_{NHAc}$=O-(3-O-(2,3,4,6-tetra-O-acetyl-D-galac-topyranosyl)-2-acetamido-4,5-di-O-benzoyl-2-deoxy-alpha-D-galactopyranosyl)

$T_s$=O-(2-acetamido-2-deoxy-3-O-(-D-galac-topyranosyl)-alpha-D-galactopyranosyl)-L-seryl

EXAMPLE 4

Immobilization of Glycopeptide Compounds on Aminated Carriers

The Compounds 7, 12, 14, 23 and 24 described in Examples 1, 2 and 3, which are in the form of methyl esters, were converted to carboxyl derivatives according to GP 15. The Compounds 10, 22, 25, 27, 30, 36 and 38 described in Examples 1, 2 and 3, which are in the form of benzyl esters, were converted to carboxyl derivatives according to GP 7 using a polar solvent such as water, methanol or methanol/ethyl acetate.

The resulting glycopeptide derivatives, which have a free carboxyl group, were coupled with aminated carriers according to GP 16 and, if appropriate, the remaining protecting group was cleaved from these products. The conventional coupling methods are described in German Patent Document No. A1-32 20 426.

EXPERIMENTAL SECTION

General Procedures (GP)

GP 1: Preparation of the peptide bond
(a) Preparation of an "active ester"

The carboxylic acid derivative (3 mmol), which has only one free carboxyl group and in which the other reactive groups are protected, was dissolved in 50 ml of dry acetonitrile. N-Hydroxysuccinimide (3 mmol) and dicyclohexyldiimide (3 mmol) were added with stirring. After 24 hours, the reaction mixture was filtered at 0° C. and the filtrate was concentrated in vacuo. The resulting syrup was used in the next reaction step without further purification.

Commonly used solvent system for thin layer chromatography: chloroform/methanol 9:1, 7:1, 3:1 and 1:1; chloroform/ethyl acetate 1:1.

(b) Preparation of a peptide bond

The amino component (3 mmol), which, apart from a free amino group, has the other reactive groups protected, was dissolved in dry chloroform (25 ml) and adjusted to pH 9 with about 3 mmol of 4-(N,N-dimethylamino)pyridine, with stirring. After 10 minutes, the "active ester" from step (a), dissolved in 25 ml of dry chloroform, was added. After 24 hours, the reaction mixture was extracted once by washing with 5% citric acid, dried with sodium sulfate and concentrated in vacuo. The resulting syrup was purified by column chromatography on silica gel.

Commonly used solvent systems for chromatography: chloroform/ethyl acetate 1:1; chloroform/acetone 7:1, 4:1 and 1:1; chloroform/methanol 9:1 and 5:1.

GP 2: Blocking and protection of the alpha-amino group of the amino acid derivatives with the DDZ protecting group The DDZ protecting group was introduced into the amino acid derivatives according to a procedure described by Ch. Birr in Int. J. Peptide Protein Res. (1979) 13, 287–295.

GP 3: Blocking and protection of the alpha-amino group of the amino acid derivatives with the BOC protecting group The BOC protecting group was introduced into the amino acid derivatives according to the procedures described in Houben-Weyl, Methoden der organischen Chemie (Methods of organic chemistry), Volume XV/I and II, published by E. Muller and E. Wunsch, 1974.

GP 4: Blocking and protection of the carboxyl or alcoholic hydroxyl group of the amino acid derivatives with the tert.-butyl protecting group The tert.-butyl protecting group was introduced into the amino acid derivatives according to the procedures described in Houben-Weyl, Methoden der organischen Chemie (Methods of organic chemistry), Volume XV/I and II, published by E. Muller and E. Wunsch, 1974.

GP 5: Blocking and protection of the carboxyl or alcoholic hydroxyl group of the amino acid derivatives with the DDBn protecting group The DDBn protecting group was bonded to the carboxyl or alcoholic hydroxyl group of the amino acid derivatives in the same manner as described in GP 4.

GP 6: Selective hydrolytic cleavage of the alpha,alpha-dimethyl-3,5-dimethoxybenzyloxycarbonyl (DDZ) protecting group from the glycopeptide The glycopeptide carrying the DDZ protecting group (3 mmol) was dissolved in 50 ml of 5% by volume trifluoroacetic acid in methylene chloride at room temperature. After stirring for 30 minutes, the solution was neutralized to pH 7 with N-methylmorpholine. The mixture was washed once with ice-water and then with dilute hydrochloric acid. The organic phase was dried with sodium sulfate and concentrated to a syrup in vacuo. The product was in the form of the hydrochloride.

A check by thin layer chromatography was carried out with the following solvent systems: chloroform ethyl acetate 1:1; chloroform/acetone 4:1 and 1:1; chloroform/methanol 4:1 and 1:1.

GP 7: Selective hydrogenolytic cleavage of the benzyl protecting group on the glycopeptide The glycopeptide carrying the benzyl protecting group (3 mmol) was dissolved in 70 ml of dry ethyl acetate and hydrogenated for 2 hours in the presence of 3.5 g of 10% palladium-on-charcoal. The mixture was then filtered, the material on the filter was rinsed and the filtrate was concentrated to a syrup in vacuo. The resulting product was purified by column chromatography. Solvents for chromatography: chloroform/acetone 4:1 and 1:1; chloroform/methanol 5:1 and 1:1.

GP 8: Selective hydrogenolytic cleavage of the benzyloxycarbonyl (Z) protecting group on the amino acid derivative The product carrying the Z protecting group (10 mmol) was hydrogenated for 1 hour in 50 ml of a mixture of ethyl acetate and methanol (1:1) in the presence of 3 g of 10% palladium-on-charcoal. The mixture was then filtered, the material on the filter was rinsed and the filtrate was concentrated in vacuo. The resulting syrup was taken up in chloroform and washed with dilute hydrochloric acid. The organic phase was dried with sodium sulfate and concentrated to a syrup in vacuo. The product, which was in the form of the hydrochloride, was purified by column chromatography on silica gel. Commonly used solvent systems for chromatography: chloroform/acetone 4:1; chloroform/methanol 5:1.

GP 9: Selective hydrolytic cleavage of the tert.-butoxycarbonyl (BOC) protecting group The product carrying the BOC protecting group (2.6 mmol) was dissolved in 10 ml of 1.2 normal hydrogen chloride in dry glacial acetic acid at room temperature. After stirring for 20 minutes, the reaction mixture was treated with 20 ml of ether and concentrated in vacuo. The resulting syrup was treated several times with toluene and concentrated until the smell of acetic acid was no longer detectable. The resulting homogeneous product was purified by column chromatography on silica gel.

Commonly used solvent systems for chromatography: chloroform/acetone 9:1 and 4:1, chloroform/methanol 9:1 and 5:1.

GP 10: Selective hydrolytic cleavage of the alpha,alpha-dimethyl-3,5-dimethoxybenzyl (DDBn) group with trifluoroacetic acid (a) The glycopeptide carrying the DDBn protecting group (3 mmol) was dissolved in 50 ml of 5% by volume trifluoroacetic acid in methylene chloride at room temperature. After stirring for 30 minutes, the solution was neutralized with N-methylmorpholine. The mixture was washed once with ice-water and then with dilute hydrochloric acid. The organic phase was dried with sodium sulfate and concentrated to a syrup in vacuo.

(b) The DDBn protecting group can also be cleaved with acids, such as HCl, in an aqueous medium. Solvent systems: chloroform/acetone 9:1, 4:1 and 1:1; chloroform/methanol 4:1 and 1:1.

GP 11: Selective reduction of the 2-azido group to the 2-amino group on the galactose unit with $NiCl_2$/$NaBH_4$ and subsequent acetylation of the amino group to the acetamido group The azide compound (1 mmol) was dissolved in ethanol (5 ml) and $NiCl_2$ solution (5 ml; 4% (w:v) of $NiCl_2.6H_2O$ in ethanol and 1% (w:v) of added boric acid) and treated with $NaBH_4$ (1 to 2 equivalents). After the reaction had ended, pyridine (5 ml) and acetic anhydride (5 ml) were added and the mixture was stirred at 20° C. for 3 to 24 hours. It was then concentrated and extracted by shaking with chloroform/water. The organic phase was dried and concentrated in vacuo.

GP 12: Selective hydrogenolysis of the 2-azido group to the 2-amino group on the galactose unit and subsequent acetylation of the amino group to the acetamido group (a) Reduction of the azido group to the amino group
Hydrogen was passed for approx. 30 minutes into a suspension of 500 mg of 10% palladium-on-charcoal and 100 ml of dry methanol. The pH of the suspension was adjusted to 7 with a mixture of methanol and aqueous concentrated sodium carbonate solution (50:1). The azide compound (5 mmol), dissolved in a small amount of methanol, was added and the mixture was then hydrogenated for 3 hours in the absence of light. In the course of the hydrogenation, the pH was monitored and, if necessary, adjusted to 7. The mixture was then filtered, the material on the filter was carefully rinsed with methanol/ether and the filtrate was concentrated to a syrup in vacuo.

(b) Acetylation
The product from step (a) was dissolved in dry methanol and treated with acetic anhydride (50 mmol). After stirring for 24 hours, the reaction mixture was concentrated in vacuo and the resulting syrup was treated several times with toluene and concentrated in vacuo. The homogeneous product was purified by column chromatography on silica gel. Commonly used solvent systems for chromatography: chloroform/acetone 9:1, 5:1 and 2:1, chloroform/methanol 9:1 and 6:1.

In the acetylation, not only the amino group of the galactose unit was converted to the acetamide group, but also, if present, the alpha-amino group of the terminal amino acid on the glycopeptide.

GP 13: Cleavage of the O-acyl protecting groups on the galactose unit of the glycopeptide The glycopeptide (2 mmol) was dissolved in 30 ml of methanol. An aqueous concentrated sodium carbonate solution was added dropwise to the methanol solution until the pH was 11. After stirring for 20 hours, the reaction mixture was neutralized with activated ion exchanger and filtered. The solution was concentrated to a syrup in vacuo and the remaining homogeneous product was purified by column chromatography.

The cleavage of the acyl protecting groups can also be carried out with catalytic quantities of sodium methylate instead of with sodium carbonate. Commonly used solvent systems for chromatography: chloroform/methanol/water 20:5:0.4 and 4:4:1.

GP 14: Cleavage of the ester-bonded gamma-tert.-butyl protecting groups on glycopeptides containing glutamic acid (a) The glycopeptide (0.7 mmol), which contains gamma-tert.-butyl glutamate units, was dissolved in 4 ml of 90% by volume aqueous trifluoroacetic acid. After 50 minutes at 20° C., 200 ml of diethyl ether were added and the precipitate was centrifuged off, washed with twice 40 ml of diethyl ether and dried.

(b) The cleavage of the gamma-tert.-butyl protecting group from glycopeptide segments containing gamma-tert.-butyl glutamate was carried out as described in GP 6. Commonly used solvent systems for chromatography: chloroform/methanol 5:1 and 3:1; chloroform/methanol water 4:4:1.

GP 15: Cleavage of the methyl ester on the spacer of the glycopeptide

A solution of the methyl ester compound (0.5 mmol) in 30 ml of 1,4-dioxane/water (9:1) was saponified, with stirring, with 1 ml portions of a 1 normal sodium hydroxide solution at 20° C. using thymophthalein as the indicator, the consumption of alkali being monitored (about 0.5 mmol of NaOH). The mixture was neutralized with the ion exchanger Dowex 50 WX-8H⁻ and filtered, the material on the filter was rinsed and the filtrate was evaporated in vacuo. The remaining homogeneous product was purified on a column of Sephadex G-25, using methanol/water (1:1) as the eluent, and lyophilized. Solvent systems for thin layer chromatography: chloroform/methanol/water 5:3:0.5 and 4:4:1.

GP 16: Binding of glycopeptide haptens carrying a spacer group to aminated carriers The glycopeptide compounds carrying a spacer group, and having a free carboxyl group capable of coupling, were coupled by known processes, either directly with carbodiimides, for example 1-ethyl-3-(3'-dimethylaminopropyl)carbodiimide hydrochloride, or as activated esters, for example N-hydroxysuccinimide derivatives, with proteins, for example bovine serum albumin, polypeptides such as polylysine, or aminated absorbents as carrier materials.

In the case of products which may still carry a protected amino acid unit such as L-Glu(gamma-tert.-butyl) or L-Glu(gamma-DDBn), the protecting group was cleaved by hydrolysis in the presence of acetic acid, trifluoroacetic acid or an aqueous mixture thereof.

| Analyses Data: |
|---|
| Compound 3 |
| 1H—NMR = (400 MHz, CD₃OD) |
| 4,78 (d, M-1 J (1,2) = 3,4 Hz) |
| 3,65 (s, CH₃O) |
| 1,37 (d, CH₃—Thr, J(CH₃, CH) = 6,7 Hz |
| Compound 4 |
| $(\alpha)_D^{20} = +97,7°$ (c = 1 in H₂O) |
| Compound 7 |
| $(\alpha)_D^{20} = +83°$ (c = 1 in H₂O) |
| 1H—NMR (400 MHz, D₂O) |
| δ = 4,85 (H—1, J(1,2) = 3,6 Hz) |
| 3,60 (COOCH₃) |
| 1,9 (CH₃O) |
| 1,32 (CH₃—Thr, J(CH₃, CH) = 6,6 Hz) |
| Compound 11 |
| $(\alpha)_D^{20} = +79,2°$ (c = 1,2 in H₂O) |
| 1H—NMR (400 MHz, D₂O) |
| δ = 4,77 (d,H—1, J(1,2) = 3,2 Hz) |
| 4,30 (d,H—1', J(1',2') = 7,7 Hz) |
| 3,56 (s,COOCH₃) |
| 1,49-1,35 (CH₂—Spacer) |
| Compound 13 |
| $(\alpha)_D^{20} = +83,2°$ (c = 1 in H₂O) |
| 1H—NMR (400 MHz, D₂O) |
| δ = 4,72 (d,H—1, J(1,2) = 3,4 Hz) |
| 4,27 (d,H—1', J(1',2') = 7,8 Hz) |
| Compound 18 |
| $(\alpha)_D^{20} = +63,7°$ (c = 1 in Chloroform) |
| 1H—NMR (400 MHz, CDCl₃): |
| δ= 8,12-7,35 (m, Ph) |
| 5,82 (d,NHAc, J(NH,2) = 9,0 Hz) |
| 4,66 (d,H—1', J(1',2') = 7,9 Hz) |
| 3,65 (CH₃O) |
| 2,06-1,90 (5 × Ac) |
| 1,62 and 1,32 (CH₂—Spacer) |
| Compound 19 |
| $(\alpha)_D^{20} = +74,0°$ (c = 1 in CHCl₃) |
| 1H—NMR (270 MHz, CDCl₃) |

| -continued |
|---|
| Analyses Data: |
| δ = 3,66 (s, OCH₃—Spacer) |
| 4,25 (d, H—1' J(1',2') = 7,8 Hz) |
| 4,82 (d, H—1, J(1,') = 3,6 Hz) |
| 5,00 (dd, H—3') |
| 5,10 (dd, H—2') |
| 5,33 (dd, H—4') |
| 5,92 (dd, H—4) |
| Compound 22 |
| $(\alpha)_D^{20} = +72,3°$ (c = 1 in MeOH/CHCl₃) |
| Compound 23 |
| $(\alpha)_D^{20} = +98,3°$ (c = 1 in CH₃OH/CHCl₃ = 3:1) |
| Compound 24 |
| $(\alpha)_D^{20} = +71,7°$ (c = 1 in CHCl₃/MeOH = 2:1) |
| 13C—NMR (90 MHz, CDCl₃/CD₃OD 2:1) |
| δ = 174-170 (6 × CO) |
| 101,1 (C—1'; β) |
| 99,0 (C—1'; α) |
| 39,39 and 39,29 (CH₂—Spacer) |
| 36,89 (Ile) |
| 33,91; 28,82 and 26,38 (CH₂—Spacer) |
| 22,15 (CH₃ Acet) |
| 15,27 (CH₃ Ile) |
| 10,89 (CH₃ Ile) |

What is claimed is:

1. A compound of the formula I, II or III

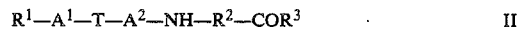

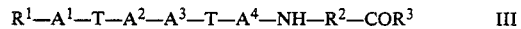

in which
R¹ denotes a hydrogen atom, an alkoxycarbonyl or arylalkoxycarbonyl group conventionally used for protecting amino groups, or CH₃—(CH₂)ₘ—CO, in which m=0-16,
R² denotes —(CH₂)ₙ— or —(CHOH)ₙ—, in which n=1-10,
R³ denotes a hydroxyl group, OCH₃, O-tert.-butyl, O-benzyl, an active ester, or a carrier,
A¹, A², A³ and A⁴ denote a valency bond or an amino acid radical selected from the group consisting of Ala, Val, Leu, Ile, Ser, Pro, Glu and Arg, in which, if appropriate, the reactive groups not forming part of the peptide bond are protected by protecting groups, and the radical T denotes

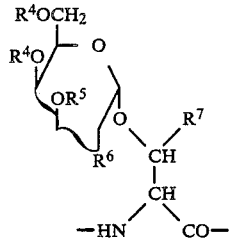

in which
R⁴ is a hydrogen atom or an acyl protecting group,
R⁵ is a hydrogen atom, an acyl protecting group or the 2,3,4,6-tetra-O-acetyl-beta-D-galactopyranosyl or beta-D-galactopyranosyl radical,
R⁶ is N₃, NH₂ or NHAc and
R⁷ is a hydrogen atom or a methyl group.

2. A compound according to claim 1 wherein said carrier is selected from the group consisting of a cephalin radical, polypeptides or proteins which carry NH groups.

3. A compound according to claim 2 wherein said carrier is a cephalin radical.

4. A compound according to claim 2 wherein said carrier is polylysine.

5. A compound according to claim 2 wherein said carrier is albumin.

6. A compound of the formula V, VI, VII, VIII, IX, X, XI, XII, XIII or XIV $R^1$—Leu—T—NH(CH$_2$)$_5$—COR$^3$      V $R^1$—Ser—T—NH(CH$_2$)$_5$—COR$^3$     VI $R^1$—Ile—T—Ser—NH(CH$_2$)$_5$—COR$^3$     VII $R^1$—Pro—T—Ala—NH(CH$_2$)$_5$—COR$^3$     VIII $R^1$—Val—T—Glu($R^9$)—NH(CH$_2$)$_5$—COR$^3$     IX $R^1$—Ile—T—Val—NH(CH$_2$)$_5$—COR$^3$     X $R^1$—Arg($R^{10}$)—T—Val—NH(CH$_2$)$_5$—COR$^3$     XI $R^1$—Ala—T—Pro—NH(CH$_2$)$_5$—COR$^3$     XII $R^1$—Val—T—Glu($R^9$)—Ile—T—Val—NH(CH$_2$)$_5$—COR$^3$     XIII $R^1$—Ile—T—Val—Arg($R^{10}$)—T—Val—NH(CH$_2$)$_5$—COR$^3$     XIV in which $R^1$ denotes a hydrogen atom or an acetyl group, $R^3$ denotes a hydroxyl group, OCH$_3$, O-tert.-butyl, O-benzyl, an active ester, a polylysine, protein or cephalin radical, a gel which carries amino groups, or a carrier, $R^9$ denotes a hydrogen atom or a protecting group for carboxyl groups, such as the methyl, benzyl or tert.-butyl group, $R^{10}$ denotes a hydrogen atom or a protecting group for amino groups, such as an NO$_2$ group, and T denotes

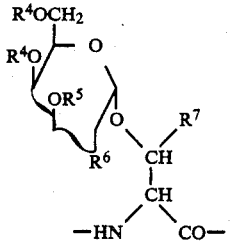

in which $R^4$ is a hydrogen atom or an acyl protecting group, $R^5$ is a hydrogen atom, an acyl protecting group or the 2,3,4,6-tetra-O-acetyl-beta-D-galactopyranosyl or beta-D-galactopyranosyl radical, $R^6$ is N$_3$, NH$_2$ or NHAc and $R^7$ is a hydrogen atom or a methyl group.

* * * * *